United States Patent [19]

Callahan

[11] 4,017,934
[45] Apr. 19, 1977

[54] MOUNTING FOR POWER TOOTHBRUSH

[76] Inventor: Harold E. Callahan, 2841 Windy Hill Road, Apt. 1147, Marietta, Ga. 30067

[22] Filed: Apr. 9, 1976

[21] Appl. No.: 675,477

[52] U.S. Cl. .............................. 15/176; 279/1 SG; 279/23 R; 403/302
[51] Int. Cl.² ........................................ A46B 13/02
[58] Field of Search ............ 15/22 R, 22 A, 22 C, 15/145, 144 R, 176; 403/301, 302, 305, 361; 279/1 Q, 1 SG, 23

[56] References Cited

UNITED STATES PATENTS

| 1,052,077 | 2/1913 | McMillan | 15/145 X |
| 1,131,863 | 3/1915 | Phillips | 279/23 X |
| 2,804,290 | 8/1957 | Kaufman | 279/1 Q |
| 3,369,265 | 2/1968 | Halberstadt et al. | 15/176 X |

Primary Examiner—Edward L. Roberts
Attorney, Agent, or Firm—Jack D. Slobod

[57] ABSTRACT

An adapter for mounting the end of a toothbrush handle to the vibratory output shaft of a toothbrush motor is a generally cylindrical body having front and rear bores for respectively receiving the handle and the shaft. The body is a resilient plastic molded about a cup-shaped metal insert. The interior surface of the insert defines the rear bore and includes roughening projections for engaging the shaft. The exterior surface of the insert appears as a pin recessed coaxially in the front bore for engaging a bore in the end of the toothbrush handle. The front bore is defined by plural angularly spaced apart plastic fingers configured to snap into a circumferential groove in the toothbrush handle.

1 Claim, 3 Drawing Figures

MOUNTING FOR POWER TOOTHBRUSH

FIELD OF THE INVENTION

The present invention relates generally to devices for attaching a toothbrush handle to vibratory output shaft of a motor unit. In its particular aspects, the present invention relates to a generally cylindrical adapter having bores at its front and rear ends for respectively grippingly receiving the handle and the shaft.

BACKGROUND OF THE INVENTION

While many techniques have heretofore been known for securing a toothbrush handle to the vibratory output shaft of a motor unit they have required special complicated configurations of the end of the motor shaft. Further, such mounting techniques on occasion did not hold the toothbrush handle securely and had projections which interferred with brushing.

OBJECTS OF THE INVENTION

It is an object of the present invention to provide an adapter for securely engaging a smooth cylindrical vibratory output shaft of a power unit at one end and for securely engaging a toothbrush handle at its other end.

It is a further object of the present invention to provide a simple and effective adapter for coupling a toothbrush handle to a vibratory motor unit.

SUMMARY OF THE INVENTION

Briefly, the aforementioned and other objects of the present invention are satisfied by providing an adaptor in the form of a generally cylindrical body having front and rear bores for respectively receiving the end of a toothbrush handle and the smooth cylindrical end of a motor shaft. The adapter is formed by a resilient plastic member molded coaxially about a cup-shaped metal insert whose interior surface forms the rear bore.

For grippingly engaging the motor shaft, plural roughening projections or ribs are provided on the interior surface.

The front bore is defined by plural angularly spaced-apart axially extending resilient fingers which are configured to snap into a circumferential groove in the handle. The exterior surface of the insert forms a pin recessed coaxially within the front bore. This pin is received in a bore in the end of the handle for centralizing the handle in the adapter and thereby aiding the fingers to provide a secure grip on the handle.

Other objects, features and advantages of the present invention will become apparent upon perusal of the following detailed description of the preferred embodiment thereof when taken in conjunction with the appended drawing wherein:

DETAILED DESCRIPTION

Figure 1:
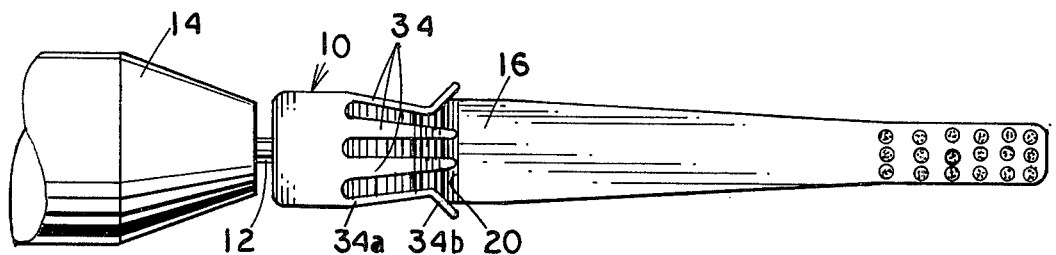
FIG. 1 is a side view of the adapter of the present invention in conjunction with a toothbrush and a motor unit.
Figure 2:
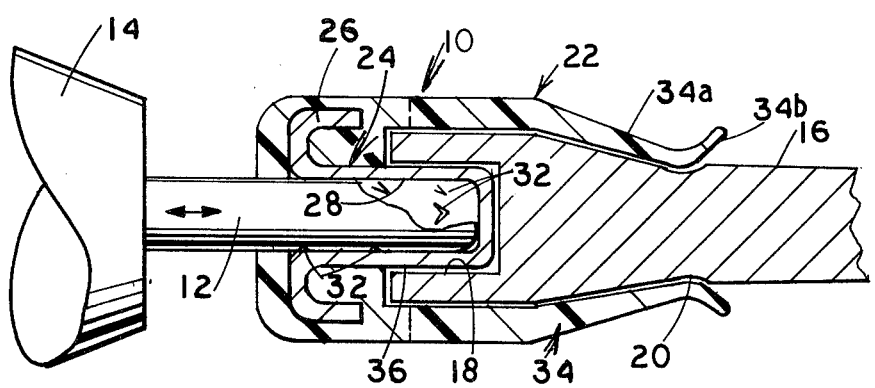
FIG. 2 is an enlarged fragmentary, cross-sectional view of FIG. 1 illustrating the adapter in detail.
Figure 3:
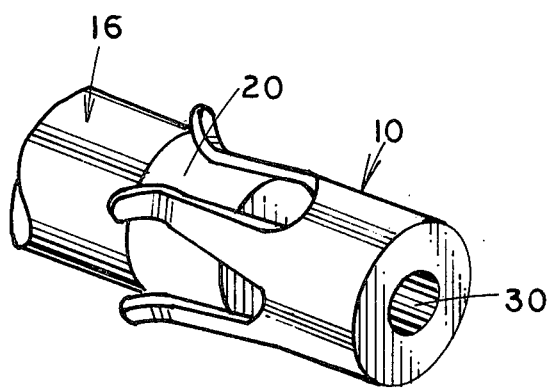
FIG. 3 is a fragmentary pictorial presentation of the adapter in conjunction with the toothbrush.

Referring to FIGS. 1 through 3 of the drawing, the adapter 10 of the present invention is illustrated for axially coupling the smooth cylindrical vibratory output shaft 12 of a motor unit 14 to the end of a toothbrush handle 16.

In accordance with the principles of the present invention the toothbrush handle 16 is provided with a central bore 18 at its free end and a circumferential groove 20 proximate the bore.

The adapter 10 is generally a cylindrical body formed by a resilient plastic body 22 such as polyethylene or polypropylene molded about a cup shaped metal insert 24 having a flange 26 for retaining the insert in the body 22. The interior surface 28 of insert 24 defines a rear axially directed bore 30 for receiving shaft 12. The surface 28 is characterized by a diameter only slightly larger than shaft 12 and has plural pointed inward projections 32 for biting into the smooth surface of shaft 12 and thereby securely frictionally engaging the shaft.

A front bore in adapter 10 for receiving handle 16 is defined by plural angularly spaced apart resilient fingers 34 of body 22 which project generally forwardly or axially. Each finger 34 includes a first portion 34a which is directed generally forwardly from the cylindrical exterior of adapter 10 but inclined somewhat radially inwardly and a second portion 34b on the end portion 34a which is directed generally forwardly but inclined somewhat radially outwardly. The junction between finger portions 34a and 34b is adapted to snap into the groove 20. The inclination of portions 34b allows the fingers 34 to be gripped manually for deflecting the fingers radially outward during insertion or removal of the toothbrush handle 16 in adapter 10.

The exterior surface 36 of insert 24 appears as a pin recessed coaxially within the front bore of adapter 10. The pin formed by surface 36 is adapted to fit slideably within the bore 18 at the end of handle 16 and thereby centralize the handle in the adapter. By utilizing this arrangement, the fingers 34 securely and independently grip handle 16.

While the preferred embodiment of the present invention has been described and illustrated in specific detail, it should be understood that numerous modifications, additions and omissions in the details thereof are possible within the intended spirit and scope of the invention claimed herein.

What is claimed is:

1. An adapter for coupling a toothbrush handle to the vibratory output shaft of a motor means, said handle having a central axially directed bore at its end and a circumferential groove proximate said end, said adapter comprising: a generally cylindrical body having front and rear bores for respectively receiving said handle and said shaft, said adapter comprising a resilient plastic body formed coaxially about a cup shaped metal insert, said rear bore being defined by the interior surface of said insert, plural roughening projections on said interior surface for frictionally engaging said shaft; said front bore being defined by plural angularly spaced axially extending fingers of said plastic body configured for snapping into said circumferential groove; a pin recessed coaxially within said front opening for engaging said bore in the end of said handle for centralizing said handle in said adapter, said pin being formed by the exterior surface of said metal insert.

* * * * *